United States Patent [19]

Nubel et al.

[11] Patent Number: 5,001,293
[45] Date of Patent: Mar. 19, 1991

[54] HALOCARBON CONVERSION

[75] Inventors: Philip O. Nubel, Naperville; Charles A. Lutman, West Chicago, both of Ill.

[73] Assignee: Amoco Corporation, Chicago, Ill.

[21] Appl. No.: 514,174

[22] Filed: Apr. 25, 1990

[51] Int. Cl.⁵ .............................. C07C 1/00; C07C 2/70
[52] U.S. Cl. ...................................... 585/408; 585/641; 585/642; 585/733
[58] Field of Search ................. 585/641, 733, 408, 642

[56] References Cited

U.S. PATENT DOCUMENTS

| | | | |
|---|---|---|---|
| 3,892,818 | 7/1975 | Scharfe et al. | 585/641 |
| 4,384,159 | 5/1983 | Diesen | 585/642 |
| 4,524,234 | 6/1985 | Kaiser | 585/642 |
| 4,652,688 | 3/1987 | Brophy et al. | 585/641 |
| 4,795,843 | 1/1989 | Imai et al. | 585/408 |

Primary Examiner—Anthony McFarlane
Assistant Examiner—Nhat Phan
Attorney, Agent, or Firm—Nick C. Kottis; William H. Magidson; Ralph C. Medhurst

[57] ABSTRACT

A method for converting halocarbons, especially lower halocarbons like chloromethane, especially methyl chloride, to hydrocarbons, especially higher molecular weight hydrocarbons, wherein a reaction mixture including the halocarbons is contacted with a borosilicate-containing catalytic composition having a specified composition in terms of mole ratios of oxides and a specified X-ray diffraction pattern to form a product mixture of the desired hydrocarbon(s).

23 Claims, No Drawings

HALOCARBON CONVERSION

BACKGROUND OF THE INVENTION

This invention relates generally to halocarbon conversion and, more specifically, to the formation of hydrocarbons from halocarbons.

As the uncertain nature of ready supplies and access to crude oil has become increasingly apparent, alternative sources of hydrocarbons and fuel have been sought out and explored. The conversion of low molecular weight alkanes (lower alkanes) to higher molecular weight hydrocarbons has received increasing consideration as such low molecular weight alkanes are generally available from readily secured and reliable sources. Natural gas, partially as a result of its comparative abundance, has received a large measure of the attention focused on sources of low molecular weight alkanes. Large deposits of natural gas, mainly composed of methane, are found in many locations throughout the world. In addition, low molecular weight alkanes are generally present in coal deposits and may be formed during numerous mining operations, in various petroleum processes, and in the above- or below-ground gasification or liquefaction of synthetic fuelstocks, such as coal, tar sands, oil shale and biomass, for example. In addition, in the search for petroleum, large amounts of natural gas are discovered in remote areas where there is no local market for its use as a fuel or otherwise. Additional major natural gas resources are prevalent in many remote portions of the world such as remote areas of western Canada, Australia, U.S.S.R. and Asia. Commonly, natural gas from these types of resources is referred to as "remote gas".

Generally, much of the readily accessible natural gas is used in local markets as the natural gas has a high value use as a fuel whether in residential, commercial or industrial applications. Accessibility, however, is a major obstacle to the effective and extensive use of remote gas. In fact, vast quantities of natural gas are often flared, particularly in remote areas from where its transport in gaseous form is practically impossible.

Conversion of natural gas to liquid products is a promising solution to the problem of transporting low molecular weight hydrocarbons from remote areas and constitutes a special challenge to the petrochemical and energy industries. The dominant technology now employed for utilizing remote natural gas involves its conversion to synthesis gas, also commonly referred to as "syngas", a mixture of hydrogen and carbon monoxide, with the syngas subsequently being converted to liquid products. While syngas processing provides a means for converting natural gas to a more easily transportable liquid that in turn can be converted to useful products, the intermediate step involved in such processing, i.e., the formation of the synthesis gas, is typically relatively costly as it involves adding oxygen to the rather inert methane molecule to form a mixture of hydrogen and carbon monoxide. While oxygen addition to the carbon and hydrogen of methane molecules may be advantageous when the desired products are themselves oxygen containing, such as methanol or acetic acid, for example, such oxygen addition is generally undesirable when hydrocarbons such as gasoline or diesel fuel are the desired products as the added oxygen must subsequently be removed. Such addition and removal of oxygen naturally tends to increase the cost involved in such processing.

Methane, the predominant component of natural gas, although difficult to activate, can be reacted with oxygen or oxygen-containing compounds such as water or carbon dioxide to produce synthesis gas. Synthesis gas can be converted to syncrude such as with Fischer-Tropsch technology and then upgraded to transportation fuels using usual refining methods. Alternatively, synthesis gas can be converted to liquid oxygenates which in turn can be converted to more conventional transportation fuels via catalysts such as certain zeolites.

Because synthesis gas processing requires high capital investment, with the syngas being produced in relatively energy intensive ways, such as by steam reforming where fuel is burned to supply heat for reforming, and represents an indirect route to the production of hydrocarbons, the search for alternate means of converting methane directly to higher hydrocarbons continues.

One such alternative method involves methane conversion to higher hydrocarbons via a "chlorine-assisted" route, such as represented by the following 2-step process:

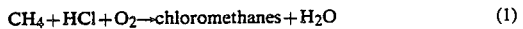

$$CH_4 + HCl + O_2 \rightarrow \text{chloromethanes} + H_2O \quad (1)$$

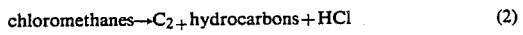

$$\text{chloromethanes} \rightarrow C_{2+} \text{hydrocarbons} + HCl \quad (2)$$

In the first step of such a process, methane (using HCl and oxygen) is chlorinated to chloromethanes. Such a chlorination step is also referred to as methane "oxychlorination" or "oxyhydrochlorination."

In the second step of such a process, chloromethanes are converted to higher hydrocarbons, e.g., hydrocarbons having 2 or more carbon atoms, represented by "$C_{2+}$", and HCl. The HCl generated in the second step can be recycled back to the first step so that effectively there is no net consumption of chlorine in the overall process.

Such a chlorine-assisted process is not yet practiced commercially.

Brothy, et al., U.S. Pat. No. 4,652,688 and Brothy, et al., U.S. Pat. No. 4,665,270 disclose processes for the conversion of monohalomethanes to hydrocarbons having at least two carbon atoms. In Brothy, et al. '688, the monohalomethane is contacted with a synthetic crystalline gallosilicate zeolite loaded either with at least one modifying cation of hydrogen, metals of Groups I to VIII of the periodic table, or with a compound of at least one Group I to VIII metal. In Brothy, et al. '270, the monohalomethane is contacted with a synthetic crystalline aluminosilicate zeolite having a silica to alumina molar ratio of at least 12:1 and containing cations of either hydrogen, copper or a metal capable of forming an amphoteric oxide, which cations are introduced either by exchange and/or by deposition, provided that when the cation is hydrogen the zeolite is Theta-1.

Butter, et al., U.S. Pat. No. 3,894,017 discloses a process for the conversion of alcohols, mercaptans, sulfides, halides and/or amines to desirable products such as aromatic hydrocarbons as well as other higher molecular weight hydrocarbons. The process utilizes a crystalline aluminosilicate zeolite catalyst having a high silica to alumina ratio of at least about 12 and a constraint index of about 1 to 12. The catalyst also preferably has a crystal density in the hydrogen form of not substantially less than about 1.6.

C. E. Taylor and R. P. Noceti, in a presentation entitled "A Process For Conversion Of Methane To Higher Hydrocarbons" presented at the 6th DOE Indirect Liquefaction Contractors' Conference in Monroeville, Pennsylvania, Dec. 3–4, 1986 reported that ZSM-5 is effective for chloromethane conversion to liquid hydrocarbons.

Noceti, et al., U.S. Pat. No. 4,769,504, discloses a process for the production of aromatic-rich, gasoline boiling range hydrocarbons from lower alkanes, particularly from methane. The process is carried out in two stages. In the first stage, an alkane is reacted with oxygen and hydrogen chloride over an oxyhydrochlorination catalyst such as copper chloride with minor proportions of potassium chloride and rare earth chloride. This produces an intermediate gaseous mixture containing water and chlorinated alkanes. In the second stage, the chlorinated alkanes are subsequently contacted with a crystalline aluminosilicate catalyst in the hydrogen or metal promoted form to produce gasoline range hydrocarbons with a high proportion of aromatics and a small percentage of light hydrocarbons ($C_2$–$C_4$). The light hydrocarbons can be recycled for further processing over the oxyhydrochlorination catalyst.

Imai, et al., U.S. Pat. No. 4,795,843 disclose treating methane with a haliding agent, such as chlorine, bromine or iodine to form a methyl halide which subsequently may be converted into usable products by contacting the halides with a conversion catalyst of silicalite, a particular type of crystalline silica material. Such a catalyst is disclosed as being less active than a crystalline aluminosilicate having a silica to alumina ratio of about 20:1 but has improved stability relative to such a crystalline aluminosilicate.

The search for alternative catalysts effective in catalyzing the conversion of halocarbons, in particular, chlorocarbons and especially chloromethanes to liquid hydrocarbons has, however, continued.

Catalytically active, crystalline borosilicate sieve catalyst is the subject of commonly assigned Klotz, U.S. Pat. No. 4,268,420; Klotz, U.S. Pat. No. 4,269,813; Klotz, et al., U.S. Pat. No. 4,285,919 and Published European Application No. 68,796. These patents disclose the preparation, characterization and utility of crystalline borosilicate catalyst and are hereby incorporated by reference.

As described in the references in the paragraph above, catalyst compositions typically are formed by incorporating an AMS-1B crystalline borosilicate molecular sieve material into a matrix such as alumina, silica or silica-alumina to produce a catalyst formulation. In one method of making AMS-1B crystalline borosilicate, sieve material is formed by crystallizing sources for silicon oxide and boron oxide with sodium hydroxide and an organic compound. After crystallization, the resulting sodium form is ion exchanged with an ammonium compound and calcined to yield the hydrogen form of AMS-1B. In another more preferred method, AMS-1B crystalline borosilicate is crystallized in the hydrogen form from a mixture containing a diamine in place of a metal hydroxide. AMS-1B borosilicates in hydrogen form are designated HAMS-1B. Typically, the hydrogen form sieve is gelled with an alumina sol, dried and calcined to yield a catalyst composition.

None of these patents, however, disclose or suggest the use of crystalline borosilicate sieve catalyst in a process for the conversion of halocarbons and, in particular, chlorocarbons to hydrocarbons.

SUMMARY OF THE INVENTION

It is an object of the present invention to overcome one or more of the problems described above.

According to the invention, a method for forming hydrocarbons from halocarbons is provided wherein a reaction mixture including halocarbons is contacted with a catalyst of a borosilicate molecular sieve material having a specified composition in terms of mole ratios of oxides and also a specified X-ray diffraction pattern, under appropriate reaction conditions, to form a product mixture including hydrocarbons.

In one embodiment of the invention, a method for converting lower chlorocarbons to higher molecular weight hydrocarbons is provided which includes the step of contacting a reaction mixture including lower chlorocarbons with a catalyst of a borosilicate molecular sieve material having a specified composition in terms of mole ratios of oxides and also a specified significant X-ray diffraction pattern, under appropriate reaction conditions, to form a product mixture including hydrocarbons having higher molecular weights than methane.

The invention also provides a method for converting chloromethane to higher molecular weight hydrocarbons. In such a method, chloromethane is contacted with a catalyst of a crystalline borosilicate and a porous refractory inorganic oxide under appropriate reaction conditions to form hydrocarbons having a higher molecular weight than methane. In the catalyst, the borosilicate and the inorganic oxide were intimately admixed with one another and the borosilicate includes a molecular sieve material having a specified composition in terms of mole ratios of oxides and also a specified significant X-ray diffraction pattern.

Also, the invention provides a method for converting methyl chloride to hydrocarbons having a higher molecular weight than methane. One such method includes the step of contacting the methyl chloride with a catalyst of crystalline borosilicate, a porous refractory inorganic oxide and a promoting amount of a promoter material of at least one element of the group of iron and gallium, under appropriate reaction conditions, to form the higher molecular weight hydrocarbons. For such catalyst, the borosilicate and inorganic oxide had been intimately admixed with one another and the borosilicate includes a molecular sieve material having a specified composition in terms of mole ratios of oxides and also a specified significant X-ray diffraction pattern.

Other objects and advantages of the invention will be apparent to those skilled in the art from the following detailed description taken in conjunction with the appended claims.

DETAILED DESCRIPTION OF THE INVENTION

The present invention provides a novel method of forming hydrocarbons from halocarbons.

While the process of the invention is described hereinafter with particular reference to the conversion of lower chlorocarbons, in particular chloromethane, especially methyl chloride, to higher molecular weight hydrocarbons (i.e., hydrocarbons having molecular weights greater than methane), such as chain hydrocarbons of 3 or more carbon atoms and aromatics, it will be apparent that the process also has application to the conversion of other chlorocarbons, such as $C_2$-$C_6$ chlorocarbons (i.e., chlorocarbons of 2 to 6 carbon atoms) to hydrocarbons, such as aromatics and chain hydrocarbons of 2 or more carbon atoms, for example. The process of the invention is believed to also have applicability to the formation of hydrocarbons from halocarbons other than chlorocarbons, e.g., halocarbons such as those containing fluorine, iodine and, in particular, those containing bromine, i.e., bromocarbons. It is to be understood, however, that at the present time the invention is perceived to have particular utility in the conversion of lower chlorocarbons such as chloromethanes, especially methyl chloride, to higher molecular weight hydrocarbons.

In the conversion of methyl chloride to hydrocarbons having a higher molecular weight than methane, the methyl chloride is contacted with a catalyst which includes a specified molecular sieve material, a crystalline borosilicate, at appropriate reaction conditions to form hydrocarbons having a higher molecular weight than methane, such as chain hydrocarbons of 3 or more carbon atoms and aromatics, for example.

Such catalytic chloromethane conversion can be performed at reaction temperatures of about 100° C. to about 600° C., preferably about 250° C. to about 450° C. In addition, the pressure which the process is effected is not, within reasonable bounds such as operation at from about 1 psig to about 10,000 psig (preferably from about 10 psig to abut 1000 psig), believed critical and may be selected in view of overall processing economics and schemes. Also, while the process will be described hereinafter with reference to operation in a continuous mode-type operation, it is to be understood that the process can be performed in a batch mode, if desired. In operation, the Weight Hourly Space Velocity (WHSV), defined as the weight of reactant feed per weight of catalyst per hour, is suitably in the range of about 0.1 to about 100 gram per gram per hour and the reactant-catalyst contact time is suitably in the range of about 0.1 second to about 100 seconds.

Also, the reaction mixture may, if desired, contain other components such as other hydrocarbons (such as $C_2$-$C_4$ hydrocarbons), oxygenated hydrocarbons (such as alcohols, ethers, etc.), inert gases (such as nitrogen, helium, etc.), carbon oxides (i.e., CO, $CO_2$), water, HCl, and other halocarbons.

The catalyst compositions used in this invention are based on AMS-1B crystalline borosilicate molecular sieve, which is described in U.S. Pat. Nos. 4,268,420, 4,269,813, and 4,285,919 and Published European Patent Application 68,796, all incorporated herein by reference. AMS-1B crystalline borosilicate generally can be characterized by the X-ray pattern listed in Table I and by the composition formula:

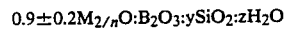

$$0.9 \pm 0.2 M_{2/n}O : B_2O_3 : y SiO_2 : z H_2O$$

wherein M is at least one cation having a valence n, y is between 4 and about 600 and z is between 0 and about 160.

TABLE I

| d-Spacing Å (1) | Assigned Strength (2) |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |

TABLE I-continued

| d-Spacing Å (1) | Assigned Strength (2) |
|---|---|
| 2.97 ± 0.02 | W-M |
| 1.99 ± 0.02 | VW-M |

(1) Copper K alpha radiation
(2) VW = very weak; W = weak; M = medium; MS = medium strong; VS = very strong The AMS-1B borosilicate molecular sieve useful in this invention can be prepared by crystallizing an aqueous mixture, at a controlled pH, of sources for cations, an oxide of boron, an oxide of silicon, and an organic template compound.

Typically, the mol ratios of the various reactants can be varied to produce the crystalline borosilicates of this invention. Specifically, the mol ratios of the initial reactant concentrations are indicated below:

|  | Broad | Preferred | Most Preferred |
|---|---|---|---|
| $SiO_2/B_2O_3$ | 5–400 | 10–150 | 10–80 |
| $R_2O^+/[R_2O^+ + M_{2/n}O]$ | 0.1–1.0 | 0.2–0.97 | 0.3–0.97 |
| $OH^-/SiO_2$ | 0.01–11 | 0.1–2 | 0.1–1 |
| $H_2O/OH^{-2}$ | 10–4000 | 10–500 | 10–500 | wherein R is an organic compound and M is at least one cation having the oxidation state n, such as an alkali or an alkaline earth metal cation or hydrogen. By regulation of the quantity of boron (represented as $B_2O_3$) in the reaction mixture, it is possible to vary the $SiO_2/B_2O_3$ molar ratio in the final product.

More specifically, the material useful in the present invention is prepared by mixing a base, a boron oxide source, and an organic template compound in water (preferably distilled or deionized water). The order of addition usually is not critical, although a typical procedure is to dissolve base and boric acid in water and then add the template compound. Generally, the silicon oxide compound is added with intensive mixing such as that performed in a Waring Blendor and the resulting slurry is transferred to a closed crystallization vessel for a suitable time. After crystallization, the resulting crystalline product can be filtered, washed with water, dried, and calcined.

During preparation, acidic conditions should be avoided. When alkali metal hydroxides are used, the values of the ratio of $OH^-/SiO_2$ shown above should furnish a pH of the system that broadly falls within the range of about 9 to about 13.5. Advantageously, the pH of the reaction system falls within the range of about 10.5 to about 11.5 and most preferably between about 10.8 and about 11.2.

Examples of materials affording silicon oxide useful in this invention include silicic acid, sodium silicate, tetraalkyl silicates and Ludox, a stabilized polymer of silicic acid manufactured by E. I. DuPont de Nemours & Co. Typically, the oxide of boron source is boric acid although equivalent species can be used such as sodium borate and other boron-containing compounds.

Cations useful in formation of AMS-1B crystalline borosilicate include alkali metal and alkaline earth metal cations such as sodium, potassium, lithium, calcium, and magnesium. Ammonium cations may be used alone or in conjunction with such metal cations. Since basic conditions are required for crystallization of the molecular sieve of this invention, the source of such cation usually is a hydroxide such as sodium hydroxide. Alternatively, form by replacing such metal cation hydroxides with an organic base such as ethylenediamine as described in Published European Application 68,796.

Organic templates useful in preparing AMS-1B crystalline borosilicate include alkylammonium cations or precursors thereof such as tetraalkylammonium compounds, especially tetra-n-propylammonium compounds. A useful organic template is tetra-n-propylammonium bromide. Diamines, such as hexamethylenediamine, can be used.

In a more detailed description of a typical preparation of this invention, suitable quantities of sodium hydroxide and boric acid ($H_3BO_3$) are dissolved in distilled or deionized water followed by addition of the organic template. The pH may be adjusted between about 11.0±0.2 using a compatible acid or base such as sodium bisulfate or sodium hydroxide. After sufficient quantities of a silica source such as a silicic acid polymer (Ludox) are added with intensive mixing, preferably the pH is again checked and adjusted to a range of about 11.0±0.2.

Alternatively, AMS-1B crystalline borosilicate molecular sieve can be prepared by crystallizing a mixture of sources for an oxide of silicon, an oxide of boron, an alkyl ammonium compound and ethylenediamine such that the initial reactant molar ratios of water to silica range from about 5 to about 25, preferably about 5 to about 20 and most preferably from about 10 to about 15. In addition, preferable molar ratios for initial reactant silica to oxide of boron range from about 4 to about 150, more preferably from about 5 to about 80 and most preferably from about 5 to about 20. The molar ratio of ethylenediamine to silicon oxide should be about above about 0.05, typically below 5, preferably between about 0.1 and about 1.0 and most preferably between about 0.2 and 0.5. The molar ratio of alkylammonium compound, such as tetra-n-propylammonium bromide, to silicon oxide can range from 0 to about 1 or above, typically above about 0.005, preferably about 0.01 to about 0.1, more preferably about 0.01 to about 0.08 and, most preferably, about 0.02 to about 0.05.

The resulting slurry is transferred to a closed crystallization vessel and reacted usually at a pressure at least the vapor pressure of water for a time sufficient to permit crystallization which usually is about 0.25 to about 20 days, typically is about one to about ten days and preferably is about one to about seven days, at a temperature ranging from about 100° C. to about 250° C., preferably about 125° C. to about 200° C. The crystallizing material can be stirred or agitated as in a rocker bomb. Preferably, the crystallization temperature is maintained below the decomposition temperature of the organic template compound. Especially preferred conditions are crystallizing at about 165° C. for about five to about seven days. Samples of material can be removed during crystallization determine the optimum crystallization time.

The crystalline material formed can be separated and recovered by well-known means such as filtration with aqueous washing. This material can be mildly dried for anywhere from a few hours to a few days at varying temperatures, typically about 50°–225° C., to form a dry cake which can then be crushed to a powder or to small particles and extruded, pelletized, or made into forms suitable for its intended use. Typically, materials prepared after mild drying contain the organic template compound and water of hydration within the solid mass and a subsequent activation or calcination procedure is necessary, if it is desired to remove this material from the final product. Typically, mildly dried product is calcined at temperatures ranging from about 260° C. to about 850° C. and preferably about 425° C. to about 600° C. Extreme calcination temperatures or prolonged crystallization times may prove detrimental to the crystal structure or may totally destroy it. Generally, there is no need to raise the calcination temperature beyond about 600° C. in order to remove organic material from the originally formed crystalline material. Typically, the molecular sieve material is dried in a forced draft oven at 165° C. for about 16 hours and is then calcined in air in a manner such that the temperature rise does not exceed 125° C. per hour until a temperature of about 540° C. is reached. Calcination at this temperature usually is continued for about 4 to 16 hours.

A catalytically active material can be placed onto the borosilicate structure, either before or after incorporation into a matrix, by ion exchange, impregnation, a combination thereof, or other suitable contact means. Before placing a catalytically active metal ion or compound on the torosilicate structure, the borosilicate should be in the hydrogen form. If the sieve was prepared using a metal hydroxide, such as sodium hydroxide, the hydrogen form typically is produced by exchange one or more times with ammonium ion, typically using ammonium acetate, followed by drying and calcination as described above.

The original cation in the AMS-1B crystalline borosilicate can be replaced all or in part by ion exchange with other cations including other metal ions and their amine complexes, alkylammonium ions, ammonium ions, hydrogen ions, and mixtures thereof. Preferred replacing cations are those which render the crystalline borosilicate catalytically active, especially for chlorocarbon conversion.

For example, ions of gallium and iron have proven to be preferred replacement cations for incorporation in catalytic compositions effective for the conversion of chloromethanes to higher molecular weight hydrocarbons, such as described above. Thus, the catalytic compositions of the invention may preferably contain a promoter material of at least one element selected from the group consisting of iron and gallium for example, as the addition of such promoter materials enhance the conversion of methyl chloride over the catalytic composition as compared to the conversion over similar compositions in the absence of such promoter materials. It being understood that by the term "promoter material," what is meant is the incorporation of the designated element in the catalyst composition in a form, such as cations of gallium or iron, for example, which results in the composition having greater catalytic activity, especially for chlorocarbon conversion, as compared to the similar composition but not containing the promoter material.

Ion exchange and impregnation techniques are well-known in the art. Typically, an aqueous solution of a cationic species is exchanged one or more times at about 25° C. to about 100° C. A hydrocarbon-soluble metal compound such as a metal carbonyl also can be used to place a catalytically active material. Impregnation of a catalytically active compound on the borosilicate or on a composition comprising the crystalline borosilicate suspended in and distributed throughout a matrix of a support material, such as porous refractory inorganic oxide such as alumina, often results in a suitable catalytic composition. A combination of ion exchange and impregnation can be used. Presence of sodium ion in a composition usually is detrimental to catalytic activity.

The amount of catalytically active material placed on the AMS-1B borosilicate can vary from about 0.01 weight percent to about 30 weight percent, typically from about 0.05 to about 25 weight percent, depending on the process use intended. (Where weight percents are in reference to the final catalyst, e.g., the borosilicate with the active material placed thereon.) The optimum amount can be determined easily by routine experimentation.

The hydrogen form of the borosilicate is typically produced by an exchange one or more times with ammonium ions, typically using ammonium acetate followed by drying and calcination as described above. The borosilicate is converted into the hydrogen form by the calcination. Alternatively, the hydrogen form of the borosilicate which is directly produced by the process according to Published European Application No. 68,796 can be used in the process of this invention. The hydrogen form of the borosilicate catalyst will be called HAMS-1B hereinafter.

The AMS-1B crystalline borosilicate useful in this invention is preferably admixed with or incorporated within various binders or matrix materials depending upon the intended process use. The crystalline borosilicate can be combined with active or inactive materials, synthetic or naturally-occurring zeolites, as well as inorganic or organic materials which would be useful for binding the borosilicate. Well-known materials include silica, silica-alumina, alumina, magnesia, titania, zirconia, alumina sols, hydrated aluminas, clays such as bentonite or kaolin, or other binders well-known in the art. Typically, the borosilicate is incorporated within a matrix material by blending with a sol of the matrix material and gelling the resulting mixture. Also, solid particles of the borosilicate and matrix material, e.g., the inorganic oxide, can be physically admixed. Typically, such borosilicate compositions can be pelletized or extruded into useful shapes. The crystalline borosilicate content can vary anywhere from a few up to 100 wt.% of the total composition. Catalytic compositions crystalline borosilicate material and preferably contain about 10 wt.% to about 95 wt.% of such material and most preferably contain about 20 wt.% to about 80 wt.% of such material.

The following examples illustrate the practice of the invention. It is to be understood that all changes and modifications that come within the spirit of the invention are desired to be protected and thus the invention is not to be construed as limited by these examples.

EXAMPLES

EXAMPLE 1

A gallium-modified borosilicate sieve catalyst having the significant X-ray diffraction lines set forth in Table I was prepared by treating a granular hydrogen form borosilicate sieve material (HAMS-1B containing 0.65 wt.% boron) with $GaCl_3$ vapor at high temperature, i.e., 460° C. Subsequently, the material was water washed at room temperature to remove remaining Cl, and dried. The gallium-modified borosilicate sieve catalyst contained 5% by weight Ga and 160 ppm B, and had a BET surface area of 254 m²/g.

EXAMPLE 2

Ga-AMS/alumina catalyst having the significant X-ray diffraction lines set forth in Table I was prepared by mixing gallium-modified borosilicate molecular sieve material (the preparation of which is described above in Example 1) with alumina sol (PHF brand), then gelling the mixture by the addition of ammonium hydroxide. The gel was dried at 120° C., extruded to form ⅛ inch extrudates and calcined at 500° C. The calcined ⅛ inch extrudates consisted of 40 wt.% Ga-AMS and 60 wt.% PHF alumina binder. The 40 wt.% Ga-AMS/alumina contained 2 wt.% Ga.

EXAMPLE 3

AMSAC-3400 catalyst having the significant X-ray diffraction lines set forth in Table I containing 40 wt.% borosilicate sieve material and 60 wt.% alumina binder in the form of 1/16 inch extrudates was calcined in air at 500° C.

EXAMPLE 4

Metal-exchanged AMSAC-3400 catalysts were prepared using 20–35 mesh AMSAC-3400 of Example 3. AMSAC-3400 catalyst (20 grams) was added to a 250 mL aqueous solution of the metal nitrate (36 g ferric nitrate nonahydrate, or 23 g zinc nitrate hexahydrate) and the mixture was stirred on a Rotovap at 80° C. for 1 hour. The catalyst was collected by filtration and washed with water (3×250 mL), and the exchange procedure (1 hour at 80° C.) was repeated using a fresh metal nitrate solution. The catalyst was then washed, dried at 120° C., and calcined in flowing air at 500° C. Elemental (ICP) analyses were obtained (with percents referring to wt.%):

Fe-AMSAC-3400: 29.6% Fe, 15.8% Si, 10.5% Al, 0.10% B

Comparative Example 1

ZSM-5/alumina catalyst was prepared in the form of 80 wt.% hydrogen form ZSM-5 sieve/20 wt.% alumina binder (⅛" pellets, sieve Si/Al ratio ~30) by mixing the ZSM-5 sieve material with alumina sol, followed by gelation with ammonium hydroxide, drying, pelletizing and calcining at 500° C.

Comparative Example 2

A gallosilicate sieve material was prepared hydrothermally (e.g., the synthesis was performed in aqueous solution and at elevated temperature similarly to the ZSM-5/alumina catalyst of Comparative Example 1 and employing gallium nitrate in place of the aluminum compound) in granular form and contained 3 wt.% Ga, 35 wt.% Si, and 300 ppm Al. This catalyst was sieved to 20–35 mesh and calcined in air at 500° C. prior to use.

Examples 5–9 and Comparative Examples 3 and 4

The materials of Examples 1–4, as well as HAMS-1B borosilicate sieve material (0.65 wt.% boron), in addition to the materials of Comparative Examples 1 and 2 were tested as catalysts for the conversion of methyl chloride using a fixed-bed, single-pass stainless steel reactor unit in Examples 5–9 and Comparative Examples 3 and 4, respectively.

Feed gas flows were controlled by mass flow controllers. Catalyst beds were supported with stainless steel helices and quartz wool packing materials. The reactor was a 16" long, ⅜" OD ss tube with a ⅛" thermowell and was operated in downflow mode. Heating was supplied by a 12" long, three-zone tube furnace. A catalyst charge of 10.0 grams was centered in the heated portion of the reactor. The methyl chloride (Matheson, 99.5%) flow rate employed was 2.0 WHSV (160 mL/min at 1 atm and 22° C.). All experiments were performed at 1 atm pressure. The unit was configured so that reactor effluent passed directly to a gas washing bottle filled with 450 mL of 6N NaOH. The purpose of the NaOH bottle, which was maintained at about 0° C., was to immediately neutralize the HCl reaction product and to condense organic liquid ($C_5+$) product. Uncondensed gases then passed to a wet test meter and to vent. Gas sampling was performed manually at a point between the NaOH bottle and the WTM.

Table II presents the results of methyl chloride conversion runs, which runs were all begun at the specified operating temperatures, with the first set of runs made at 300° C. (Note: All reported run temperatures are internal catalyst bed temperatures measured using thermowell in the reactor interior. Catalyst bed temperatures were reasonably uniform throughout the length of the bed, usually varying by less than 5° C. from the desired value. Also note that furnace temperature settings were slightly lower than the catalyst bed temperatures due to the exthermicity of the reaction.) After initiating methyl chloride flow, a 2-hour period was allowed for reactor line-out and saturation of the NaOH solution with effluent gases. Organic condensate was removed from the NaOH scrubber, and a 4-hour sample period was initiated. At the end of this period gas sampling was performed and the liquid organic product (condensate in the NaOH bottle) was collected and weighed. The unit was purged with $N_2$ flow overnight, the temperature was raised, and the next day a similar $CH_3Cl$ run was performed at 350° C. Runs at 400° C. were performed on the following day after another overnight $N_2$ purge. Gas samples were analyzed for $CH_3Cl$ and other organics using a Flame Ionization Detector (FID) GC. Since HCl was not quantified, conversions and mass balances were calculated using the assumption that one mole of HCl is generated for every mole of reacted $CH_3Cl$. Mass balances thus calculated were typically from 95–105% (weight of total effluent, including HCl, divided by feed weight).

The results are presented in Table II below.

TABLE II

| Conversion of Methyl Chloride Over Molecular Sieve Catalysts | | | | |
|---|---|---|---|---|
| Ex. | Catalyst | 300° C. | 350° C. | 400° C. |
| | | Initial $CH_3Cl$ Conversion (%) | | |
| 5 | Ga-AMS, 5 wt. % Ga | 63 | 81 | — |
| 6 | Ga-AMS/alumina (40 wt. % Ga-AMS) | 45 | 60 | 58 |
| 7 | AMSAC-3400 | 30 | 38 | 35 |
| 8 | Fe-AMSAC-3400 (30 wt. % Fe) | 65 | 60 | — |
| 9 | HAMS-1B | <5 | <10 | — |
| C3 | ZSM-5/alumina (80 wt. % ZSM-5) | 38 | 64 | 83 |
| C4 | Gallosilicate sieve, 3 wt. % Ga | 30 | 59 | 78 |
| | | $C_5+$ (%) Hydrocarbon Selectivity | | |
| 5 | Ga-AMS, 5 wt. % Ga | 71 | 62 | — |
| 6 | Ga-AMS/alumina (40 wt. % Ga-AMS) | 62 | 51 | 32 |
| 7 | AMSAC-3400 | 61 | 55 | 37 |
| 8 | Fe-AMSAC-3400 (30 wt. % Fe) | 69 | 61 | — |
| 9 | HAMS-1B | — | — | — |
| C3 | ZSM-5/alumina (80 wt. % ZSM-5) | 58 | 51 | 51 |
| C4 | Gallosilicate sieve, 3 wt. % Ga | 55 | 56 | 50 |

DISCUSSION

The results in Table II clearly indicate that the gallium-incorporated borosilicate catalysts (Ex. 5 and Ex. 6) were substantially more active for methyl chloride conversion than the HAMS-1B sieve material (Ex. 9). In addition, the catalysts of Ex. 5 and Ex. 6 were markedly more active than AMSAC-3400 (Ex. 7). Also, the Fe-AMSAC catalyst (Ex. 8) was much higher in activity than unmodified AMSAC-3400.

The results in Table II also show that the activities of the gallium- and iron-promoted borosilicate catalyst compositions, (Ga-AMS, Ga-AMS/alumina, and Fe-AMSAC-3400) compare favorably to those of ZSM-5 (Comparative Ex. 3) and the gallosilicate sieve (Comparative Ex. 4), with the gallium and iron-promoted borosilicate catalyst compositions of the invention generally providing superior initial $CH_3Cl$ conversions and $C_5+$ hydrocarbon selectivities than the catalyst materials of the comparative examples, particularly in conjunction with operation at lower temperatures, such as operation at temperatures less than 400° C., e.g., operation at a temperature of about 350° C. and especially operation at a temperature of about 300° C.

The foregoing detailed description is given for clearness of understanding only, and no unnecessary limitations are to be understood therefrom, as modifications within the scope of the invention will be obvious to those skilled in the art.

What is claimed is:

1. A method for forming hydrocarbons from halocarbons comprising the step of:

contacting a reaction mixture comprising halocarbons with a catalytic composition under appropriate reaction conditions to form a product mixture comprising hydrocarbons, said catalytic composition comprising a borosilicate molecular sieve material having the following composition in terms of mole ratios of oxides:

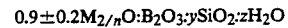

$0.9 \pm 0.2 M_{2/n}O : B_2O_3 : y SiO_2 : z H_2O$ wherein M is at least one cation having a valence n, y is between 4 and about 600, and z is between 0 and about 160 and having the significant X-ray diffraction pattern set forth in Table I.

2. The method of claim 1 wherein said catalytic composition additionally comprises a promoter material of at least one element selected from the group consisting of iron and gallium.

3. The method of claim 1 wherein said reaction mixture consists essentially of halocarbons.

4. The method of claim 1 wherein said halocarbons comprise bromocarbons.

5. The method of claim 1 wherein lower halocarbons are converted to higher molecular weight hydrocarbons.

6. The method of claim 5 wherein said lower halocarbons comprise methyl chloride and said higher molecular weight hydrocarbons comprise $C_3+$ hydrocarbons.

7. The method of claim 2 wherein lower halocarbons are converted to higher molecular weight hydrocarbons.

8. The method of claim 7 wherein said lower halocarbons comprise methyl chloride and said higher molecular weight hydrocarbons comprise $C_{3+}$ hydrocarbons.

9. The method of claim 8 wherein said reaction mixture consists essentially of methyl chloride.

10. A method for converting lower chlorocarbons to higher molecular weight hydrocarbons comprising the step of:

contacting a reaction mixture comprising lower chlorocarbons with a catalytic composition under appropriate reaction conditions to form a product mixture comprising hydrocarbons having higher molecular weights than methane, said catalytic composition comprising a borosilicate molecular sieve material having the following composition in terms of mole ratios of oxides:

$$0.9\pm0.2M_{2/n}O:B_2O_3:ySiO_2:zH_2O$$

wherein M is at least one cation having a valence between 4 and about 600, and z is between 0 and about 160 and having the significant X-ray diffraction pattern set forth in Table I.

11. The method of claim 10 wherein said catalytic composition additionally comprises a promoter material of at least one element selected from the group consisting of iron and gallium.

12. The method of claim 11 wherein said lower chlorocarbons comprise methyl chloride and said higher molecular weight hydrocarbons comprise $C_{3+}$ hydrocarbons.

13. The method of claim 10 wherein said lower chlorocarbons comprise methyl chloride and said higher molecular weight hydrocarbons comprise $C_{3+}$ hydrocarbons.

14. The method of claim 10 wherein said reaction mixture consists essentially of lower chlorocarbons comprising methylchlorde.

15. A method for converting chloromethane to higher molecular weight hydrocarbons comprising the step of:

contacting chloromethane with a catalytic composition under appropriate reaction conditions to form hydrocarbons having a higher molecular weight than methane, said catalytic composition comprising a crystalline borosilicate and a porous refractory inorganic oxide, said borosilicate and said inorganic oxide having been intimately admixed with one another, said borosilicate comprising a molecular sieve material having the following composition in terms of mole ratios of oxides:

$$0.9\pm0.2M_{2/n}O:B_2O_3:ySiO_2:zH_2O$$

wherein M is at least one cation having a valence n, y is between 4 and about 600, and z is between 0 and about 160 and having the significant X-ray diffraction pattern set forth in Table I.

16. The method of claim 15 wherein said catalytic composition additionally comprises a promoting amount of a promoter material of iron.

17. The method of claim 15 wherein said catalytic composition additionally comprises a promoting amount of a promoter material of gallium.

18. The method of claim 15 wherein said chloromethane comprises methyl chloride and the higher molecular weight hydrocarbons comprise $C_{3+}$ hydrocarbons.

19. A method for converting methyl chloride to hydrocarbons having a higher molecular weight than methane, said method comprising the step of:

contacting the methyl chloride with a catalytic composition under appropriate reaction conditions to form said hydrocarbons, said catalytic composition comprising crystalline borosilicate, a porous refractory inorganic oxide, and a promoting amount of a promoter material of at least one element selected from the group consisting of iron and gallium, said borosilicate and said inorganic oxide having been intimately admixed with one another, said borosilicate comprising a molecular sieve material having the following composition in terms of mole ratios of oxides:

$$0.9\pm0.2M_{2/n}O:B_2O_3:ySiO_2:zH_2O$$

wherein M is at least one cation having a valence n, y is between 4 and about 600, and z is between 0 and about 160 and having the significant X-ray diffraction pattern set forth in Table I.

20. The method of claim 19 wherein said promoter material is of the element iron and said promoting amount is in the range of about 0.05 weight percent to about 25 weight percent.

21. The method of claim 19 wherein said promoter material is of the element gallium and said promoting amount is in the range of about 0.05 weight percent to about 25 weight percent.

22. The method of claim 19 wherein the operating temperature for the reaction is less than about 400° C.

23. The method of claim 22 wherein the operating temperature of the reaction is in the range of about 300° C. to about 350° C.

* * * * *

UNITED STATES PATENT OFFICE
CERTIFICATE OF CORRECTION

Patent No. 5,001,293      Dated March 19, 1991

Inventor(s) Philip O. Nubel, Charles A. Lutman

It is certified that error appears in the above-identified patent and that said Letters Patent is hereby corrected as shown below:

| Col. | Line | |
|---|---|---|
| 5 | 29 | "abut" should be --about-- |
| 7 | 1 | "form" should be --formed-- |
| 7 | 56 | "crystallization determine" should be --crystallization to determine-- |
| 8 | 22 | "torosilicate" should be --borosilicate-- |
| 13 | 24-25 | "valence between 4 and about 600" should be --valence n, y is between 4 and about 600,-- |
| 13 | 42 | "methylchlorde" should be --methyl chloride-- |

Signed and Sealed this

Twenty-second Day of September, 1992

*Attest:*

DOUGLAS B. COMER

*Attesting Officer*      *Acting Commissioner of Patents and Trademarks*